United States Patent
Jackson

(10) Patent No.: US 6,970,256 B1
(45) Date of Patent: Nov. 29, 2005

(54) APPARATUS AND METHODS FOR MEASURING THICKNESS AND REFRACTIVE INDEX

(76) Inventor: John H. Jackson, 13 Baldwin St., Pennington, NJ (US) 08534

( * ) Notice: Subject to any disclaimer, the term of this patent is extended or adjusted under 35 U.S.C. 154(b) by 282 days.

(21) Appl. No.: 10/414,785

(22) Filed: Apr. 16, 2003

(51) Int. Cl.[7] .............................................. G01N 21/55
(52) U.S. Cl. ..................... 356/630; 356/445
(58) Field of Search ................ 356/625, 630, 356/445–448, 136

(56) References Cited

U.S. PATENT DOCUMENTS

| | | | |
|---|---|---|---|
| 5,237,392 A * | 8/1993 | Hickel et al. ................ | 356/630 |
| 5,351,127 A * | 9/1994 | King et al. ................... | 356/445 |
| 5,565,978 A * | 10/1996 | Okubo et al. ................ | 356/128 |
| 6,549,276 B1 * | 4/2003 | Longtin ....................... | 356/128 |
| 2004/0235177 A1 * | 11/2004 | Guedon et al. ................ | 436/5 |

OTHER PUBLICATIONS

Metricon® Corporation, "Model 2010 Prism Coupler-Major Application Areas", Jan. 1997, www.metricon.com, 2 pages.
"Characterize with a Wave-Guide Coupler", Back to Basics Analytical Instrumentation, *R & D Magazine*, Dec. 2000, 55, www.rdmag.com.

\* cited by examiner

Primary Examiner—Michael P. Stafira
(74) Attorney, Agent, or Firm—Woodcock Washburn LLP

(57) ABSTRACT

Apparatus and methods for determining thickness and refractive index of thin films and bulk materials are provided. Such apparatus may include a sample support adapted to hold a sample in close contact with the base of a prism, a thermal controller that regulates the temperature of the sample, a light source operable to direct incident light at a variety of incident angles the base of the prism, and a detector positioned to receive output light from the prism. The output light has intensity variations as a function of incident angle. Sample thickness and refractive index may be determined from the intensity variations.

50 Claims, 3 Drawing Sheets

APPARATUS AND METHODS FOR MEASURING THICKNESS AND REFRACTIVE INDEX

FIELD OF THE INVENTION

The invention relates to apparatus and methods for measuring sample thickness and refractive index. More particularly, the invention relates to apparatus and methods for measuring thickness and refractive index of thin films and bulk materials at various temperatures.

BACKGROUND OF THE INVENTION

Devices for measuring thickness and refractive index of thin films and bulk materials at room temperature are well known. FIG. 1 depicts such a device 10, of which the "METRICON®" Model 2010 "PRISM COUPLER" is an example.

In such a device, a sample 30 is brought into close contact with the base 12B of a prism 12. Typically, a small air gap 18 will form between the sample 30 and the prism 12. As depicted in FIG. 1, the sample 30 may be a film 32 supported by a substrate 34. The sample 30 may be brought into contact with the base 12B of the prism 12 via a coupling mechanism 14, which may have a coupling head 14A as shown.

Incident light 20 is directed onto an entrance face 12A of the prism 12. The incident light 20 encounters the entrance face 12A at an angle θ and is typically deflected as it enters the prism 12. The deflected light 22 travels through the prism 12 and strikes the base 12B of the prism 12 at an angle of incidence $\theta_1$ (which, as shown in FIG. 1, may be measured relative to the normal axis z, i.e., the axis perpendicular to the base 12B of the prism 12). The reflected light 24 travels through the prism 12 and exits the exit face 12C of the prism 12. The reflected light 24 is typically deflected as it exits the prism 12. A detector 16, which may be a single photodetector element or an array of photodetector elements, such as a CCD, for example, is situated proximate the exit face 12C of the prism 12. The detector 16 receives the deflected reflected light 26.

At most angles of incidence $\theta_1$, the deflected light 22 will be nearly totally reflected at the prism base 12B. However, at certain angles of incidence $\theta_1$ on the base 12B of the prism 12, light 36 will couple efficiently into the film 32 and propagate down the film 32 in an optical propagation or substrate mode. An optical propagation mode occurs when the film 32 is on a substrate or underlying film of lower refractive index. A substrate mode occurs when the film 32 is on a substrate of higher index. These angles, which are known as "mode angles," are related to the thickness and index of the film 32. At the mode angles, where light 36 is coupled into the film 32, the light 26 reflected to the detector 16 on the exit side 12C of the prism 12 is reduced (see FIG. 2). This provides a mechanism for detecting the optical or substrate propagation mode. Detection of two modes allows calculation of film thickness and index (two equations in two unknowns). If the film possesses more than two modes, each pair of modes allows an additional independent estimate of thickness and index to be made. Any of a number of well-known mechanisms may be provided for varying the incident angle of the light.

There are many applications in which the sample is to be used in an environment where the temperature may differ, sometimes significantly, from room temperature. For example, the sample might be designed for outdoor use (e.g., automotive, electrical supply, etc.). For such an application, it may be desirable to determine thickness and index at temperatures below room temperatures. In other applications, such as packaged electronic devices, for example, the sample might be designed to operate in a heated environment. For such an application, it may be desirable to determine thickness and index at temperatures up to 200° C. or more.

In the prism coupling technique, measurement of index at elevated temperature is complicated by the fact that the sample being measured is in intimate contact with the prism on the front side and the coupling mechanism on the back. Temperature gradients across the prism/sample/coupling mechanism interface create uncertainty in the temperature of the sample. In addition, accurate knowledge of the prism index is required for accurate sample measurements because the refractive index of the prism also changes with temperature. Any gradient in the prism temperature causes uncertainty in the prism index at the point of coupling into the sample, which affects measurement accuracy.

It would be desirable, therefore, if apparatus and methods were provided for measuring thickness and refractive index of thin films and bulk materials at temperatures other than room temperature. Such apparatus and methods would be particularly useful if they were operable to determine thickness and/or index of refraction of such samples at various temperatures.

SUMMARY OF THE INVENTION

The invention provides apparatus and methods for measuring thickness and refractive index of thin films and bulk materials at various temperatures. Apparatus according to the invention includes a thermal controller that regulates the temperature of the sample by providing heating or cooling of the sample to a prescribed temperature. Thermal elements are optimally located to minimize temperature gradients across the sample. A temperature sensor in contact with the prism may be used to control the temperature of the prism and, thereby, the temperature of a first surface of the sample. Another temperature sensor in contact with a sample support may be used to control the temperature of the sample support and, thereby, the temperature of an opposing surface of the sample. By maintaining the temperature of the sample support at the same temperature as the prism, temperature gradients across the sample are effectively eliminated.

Apparatus according to the invention allows determination of temperature coefficient of refractive index by measuring index for thin films and bulk materials at temperatures other than room temperature. Temperature coefficient data can also be used to calculate thermal expansion coefficients.

BRIEF DESCRIPTION OF THE DRAWINGS

Certain preferred embodiments of the invention will now be described in detail with reference to the figures. Those skilled in the art will appreciate that the description given herein with respect to the figures is for exemplary purposes only and is not intended in any way to limit the scope of the invention.

DETAILED DESCRIPTION OF ILLUSTRATIVE EMBODIMENTS

Figure 3:
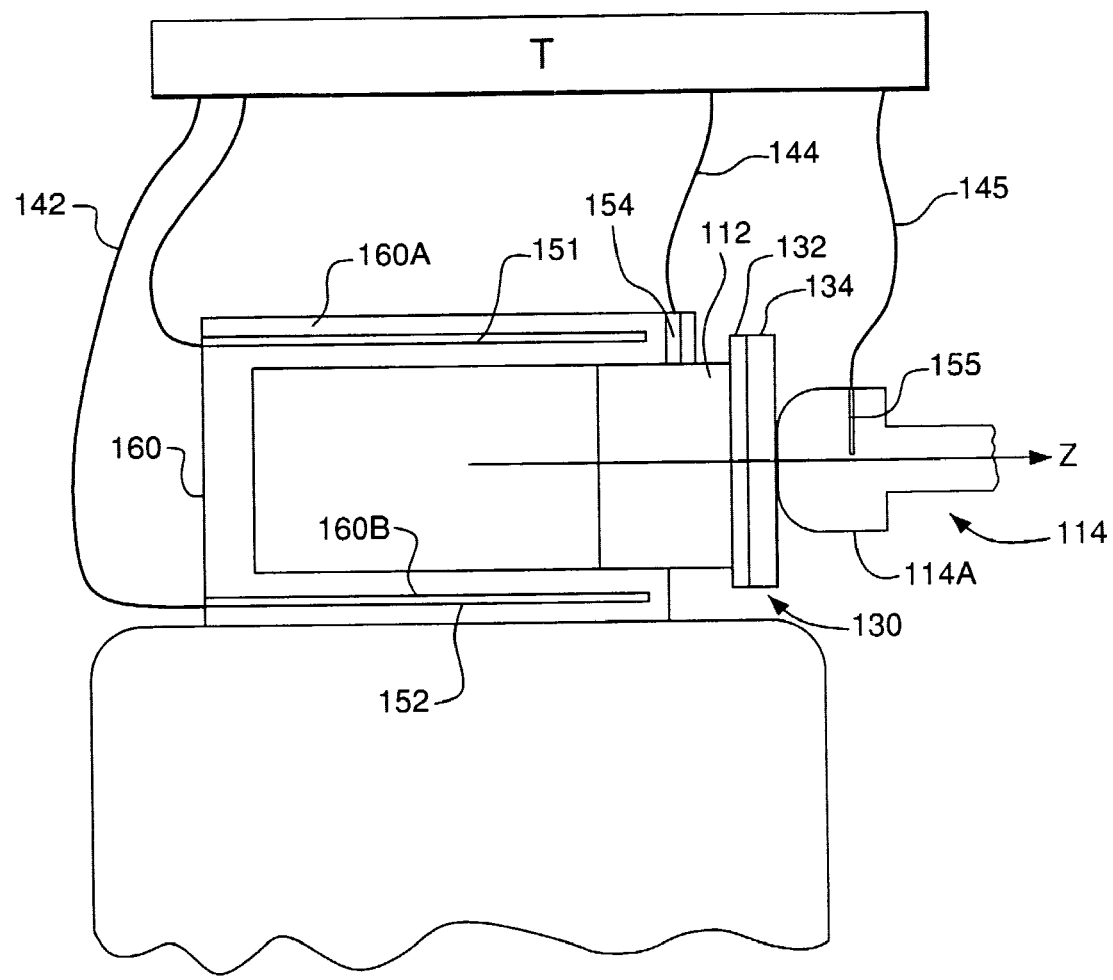
FIG. 3 is a side view cross-section of a preferred embodiment of apparatus according to the invention for measuring thickness and refractive index of thin films at variable temperatures.
Figure 4:
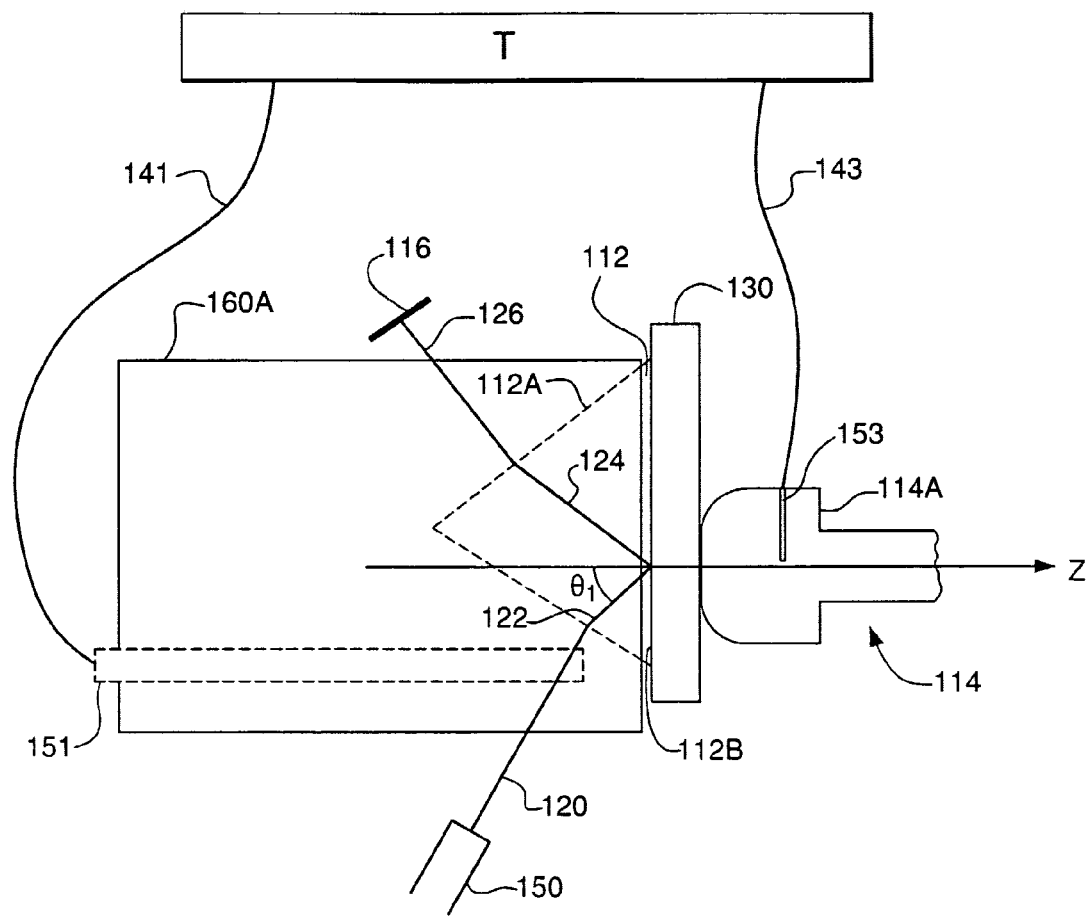
FIG. 4 is a top view cross-section of a preferred embodiment of apparatus according to the invention for measuring thickness and refractive index of thin films at various temperatures.

FIG. 3 is a side view and FIG. 4 is a top view of a preferred embodiment of apparatus 100 according to the invention for measuring thickness and/or refractive index of thin films and bulk materials at various temperatures. As shown, a sample 130 is brought into close contact with the base 112B of a prism 112. Typically, a small air gap will form between the sample 130 and the prism 112. As depicted in FIG. 3, the sample 130 may be a film 132 supported by a substrate 134. The film 132 may be a thin film or a multilayer film, where the film layer to be measured is disposed on a film layer of lower index.

A sample support 114 is provided to support the sample 130. The sample support 114 may be a fixed support on which the sample 130 is allowed to rest or a movable support. If the sample support 114 is fixed, the prism 112 may be moved to make contact with the sample 130. If the sample support 114 is movable, the sample support 114 may be moved to put the sample 130 into contact with the prism 112. In a preferred embodiment, the sample support 114 may include a rounded surface and a coupling mechanism that provides sufficient force to drive a small part of the sample 130 into close contact with the prism 112. Such a coupling mechanism may be manually, mechanically, or pneumatically operated. Though a pneumatically-operated coupling mechanism is preferred, a micrometer or screw, for example, may be used to advance either the sample 130 or prism 112 until contact is made. Similarly, the prism 112 and sample 130 may be pushed into close contact by hand.

Incident light 120 is directed at an angle θ onto an entrance face 112A of the prism 112. Preferably, the incident light 20 is monochromatic and, typically, though not necessarily, will be laser light. Alternatively, a wide band white light source, such as an arc lamp, could be used, with the wideband light filtered to a narrow range of wavelengths. The system may include multiple lasers of different wavelengths or, for a wideband source, multiple narrowband filters to enable measurement of index at a variety of wavelengths.

Figure 1:
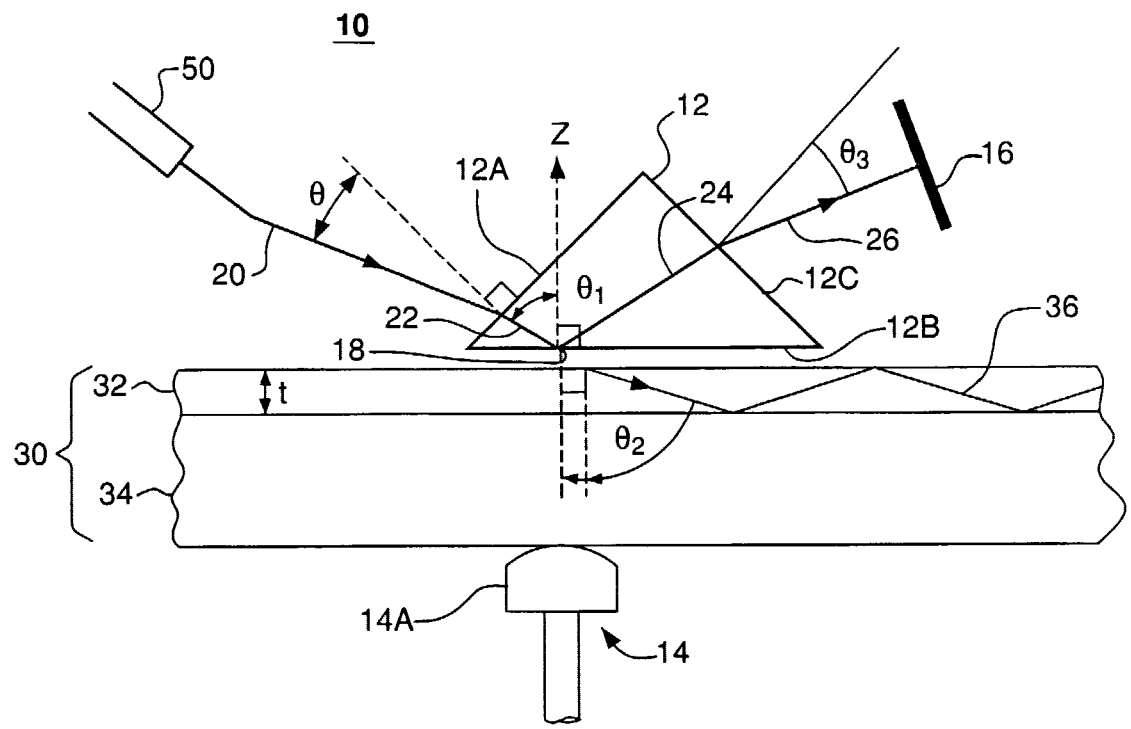
FIG. 1 depicts prior art apparatus for measuring thickness and refractive index of thin films.
Figure 2:
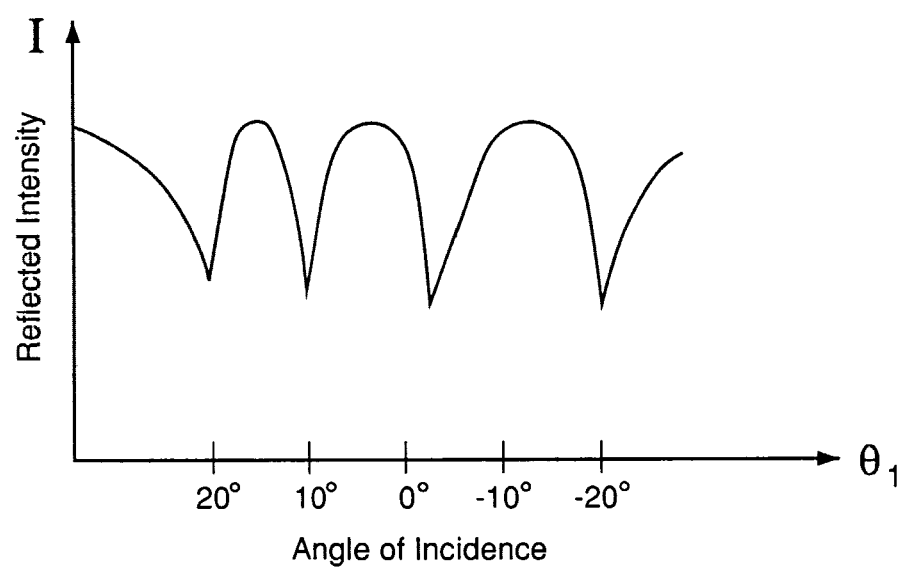
FIG. 2 is a plot of reflected light intensity as a function of angle of incidence.

The incident light 120 is typically deflected as it enters the prism 112. The deflected light 122 travels through the prism 112 and strikes the base 112B of the prism 112 at an angle of incidence $\theta_1$ to the normal axis z (i.e., the axis perpendicular to the base 112B of the prism 112). The reflected light 124 travels through the prism 112 and exits the exit face 112C of the prism 112. The reflected light 124 is typically deflected as it exits the prism 112. A detector 116, which may be a single photodetector element or an array of photodetector elements, such as a CCD, for example, is situated proximate the exit face 112C of the prism 112. The detector 116 receives the deflected reflected light 126. As described in detail above, at most angles of incidence $\theta_1$, the deflected light 122 will be nearly totally reflected at the prism base 112B. However, at the mode angles, the intensity of light 126 reflected to the detector 116 is reduced (see FIG. 2).

The number of modes supported by a film of given index increases with film thickness. If the film 132 is thick enough to support more than two propagation modes, thickness t and index η may be calculated, using well-known techniques, for each pair of modes. An average and standard deviation can then be calculated for each of these multiple estimates.

Any of a number of techniques may be used for providing light at various incident angles. For example, the prism 112 may be coupled to a rotary table that may be used to vary the incident angle $\theta_1$. The rotary table may be rotated by hand or by a motor under manual or computer control. Alternatively, the light source 150 may be adapted to move in an arc around the prism 112. In another embodiment, a cone of light may be focused onto the base of the prism. Such a cone of light has a broad range of incident angles, i.e., broad enough to excite more than one propagation mode. Thus, certain rays (at certain angles of incidence) within the cone simultaneously excite the modes. A reflected cone of light at the exit side of the prism has one narrow dark line for each mode. A position sensitive detector array may be used to sense the locations of the dark lines due to the modes. In such an approach, no rotation of the prism is required, as the cone of light provides various angles of incidence. It is sometimes possible to observe all the modes of a sample by directing a collimated light source onto the prism base at one of the mode angles. Light is then scattered from this excited mode into all the other modes and a series of bright lines (one for each mode) is then observed at the detector or detector array.

Preferably, the prism 112 is disposed between a pair of prism supports 160A, 160B, each of which is made of a thermally conductive material. The prism may be held in place between the prism supports 160A, 160B via an adhesive such as an epoxy, for example. In a preferred embodiment, the prism supports 160A, 160B are clamp jaws. That is, the prism 112 may be held between the jaws 160A, 160B of a clamp 160. The clamp 160 may be fixedly coupled to a platform 166, which may be rotatable.

A thermal controller T is provided to control the temperature of the sample 130. Preferably, the thermal controller is adapted to heat and/or cool the sample to a prescribed temperature. A thermal element 153 and temperature sensor 155 are employed in the sample support 114, and are aligned as nearly as possible to the contact point with the prism 112. Preferably, the thermal element 153 and temperature sensor 155 are received into respective bores in the sample support 114. The bores extend into the sample support to points on or near the contact point with the prism 112. The thermal element 153 is adapted to heat and/or cool the sample support 114 near the contact point with the prism 112.

Similarly, the thermal controller T is adapted to regulate the temperature of the prism 112 by regulating respective temperatures of each of the prism supports 160A, 160B. Respective thermal elements 151, 152 are employed in each of the prism supports, such as in the jaws of a clamp 160. The thermal elements 151, 152 are adapted to heat and/or cool the prism supports 160A, 160B near the contact points with the prism 112. By maintaining the prism supports 160A, 160B at nearly the same temperature, the prism 112 is also maintained at that temperature. A temperature sensor 154 is employed to determine the temperature of the prism 112. The thermal controller T determines from the current temperatures of the prism 112 and the sample support 114 whether to provide additional heating or cooling to the prism supports 160A, 160B or the sample support 114.

Thermal elements 151, 152, and 153 could be resistive wire heating cartridges, for example, which could be used for heating, or thermoelectric elements, such as "Peltier elements," which could be used for heating and/or cooling. Respective thermal conductors 141, 142, 143 couple the thermal controller T to the respective thermal elements 151, 152, 153. Similarly, respective electrical conductors 144, 145 couple the thermal controller T to the respective temperature sensors 154, 155. Preferably, the temperature sensors are thermocouples, though they could be thermistors or other such resistance temperature detectors. It should be understood that a single thermal controller T may be employed, or separate thermal controllers may be employed to regulate the respective temperatures of each of the prism supports 160A, 160B and the sample support 114.

When the prism 112 and sample support 114 are maintained at a common temperature, a near-zero temperature gradient exists through the sample 130 along the axis z between the sample support 114 and the prism 112. It is preferred that the sample support 114 and prism supports 160A, 160B are made of materials having high thermal conductivity (e.g., metals) in order to reduce the temperature gradients within them. Thus, the temperature of the sample 130 along the z-axis is nearly same as the common temperature of the prism 112 and the sample support 114.

To reduce temperature gradients across the sample and the prism, it is desirable to design as much symmetry as possible into the system. For example, the clamp 160 should be as symmetrical as possible about the prism 112 and the thermal elements 151, 152, 153 should be symmetrically located so that the prism 112 is in the center of the symmetry. Careful design in the location of thermal insulation may also be employed to reduce temperature gradient effects and enables the heating of only a very small mass. As a result, the total thermal load on the system may be less than 20 watts and the temperature of the rest of the system unaffected. For example, in a preferred embodiment, the material above the clamp 160 may be a thermally insulating material (e.g., air). Consequently, it is preferred that the platform 166 is made of a thermally insulating material. As a result, a near-zero temperature gradient can be achieved across the prism 112. This is desirable because accurate measurement of sample index requires accurate knowledge of prism index vs. temperature. Once the temperature coefficient for the prism has been specified, and the temperature of the prism is accurately known, the refractive index of the prism may be correctly determined.

The above-described apparatus and methods may also be used to measure the refractive index where the sample is a bulk material, such as a glass or polymer, for example. At angles of incidence above the critical angle for the prism/bulk material interface, the monochromatic light is totally reflected at the base of the prism. At angles below the critical angle some of the light is refracted into the bulk sample and the light reaching the detector or detector array on the far side of the prism is reduced. By finding the angular location of this critical angle, the index of the bulk material can be determined.

Though the invention has been described herein in connection with certain currently preferred embodiments shown in the several figures, it should be understood that other similar embodiments may be used or modifications and additions may be made to the described embodiments for practicing the invention without deviating therefrom. Therefore, the invention should not be limited to any particular embodiments, but rather construed in breadth and scope in accordance with the recitation of the appended claims.

What is claimed:

1. Apparatus for determining thickness and refractive index, comprising:
    a prism having a base;
    a sample support adapted to hold a sample in close contact with the prism base;
    a thermal controller that regulates the temperature of the sample;
    a first temperature sensor that provides to the thermal controller an indication of a current temperature of the prism;
    a light source operable to direct incident light to the base of the prism; and
    a detector positioned to receive from the prism output light having intensity variations, wherein at least one of sample thickness and refractive index may be determined from the intensity variations.

2. Apparatus according to claim 1, wherein the thermal controller regulates respective temperatures of the prism and the sample support.

3. Apparatus according to claim 1, wherein the light source includes a monochromatic light source.

4. Apparatus according to claim 1, wherein the detector comprises an array of photodetector elements.

5. Apparatus according to claim 1, wherein the first temperature sensor comprises a thermocouple.

6. Apparatus according to claim 1, further comprising:
    a second temperature sensor that provides to the thermal controller an indication of a current temperature of the sample support.

7. Apparatus according to claim 6, wherein the second temperature sensor comprises a thermocouple.

8. Apparatus according to claim 1, wherein the thermal controller enables the respective temperatures of the prism and the sample support to be set to a common temperature.

9. Apparatus according to claim 1, wherein the prism is disposed between a pair of prism supports, each of which is made of a thermally conductive material.

10. Apparatus according to claim 9, wherein the thermal controller is adapted to regulate the temperature of the prism by regulating respective temperatures of each of the prism supports.

11. Apparatus according to claim 10, wherein the thermal controller is adapted to regulate the respective temperatures of the prism supports via a respective thermal element in each of the prism supports.

12. Apparatus according to claim 11, wherein the prism supports are clamp jaws.

13. Apparatus according to claim 1, wherein the thermal controller is adapted to regulate the temperature of the sample support.

14. Apparatus according to claim 13, wherein the thermal controller is adapted to regulate the temperature of the sample support via a thermal element in the sample support.

15. Apparatus according to claim 1, wherein the thermal controller is adapted to heat the sample to a temperature above room temperature.

16. Apparatus according to claim 1, wherein the thermal controller is adapted to cool the sample to a temperature below room temperature.

17. Apparatus for determining thickness and refractive index, comprising:
    a prism held between a pair of thermally conductive prism supports;
    a coupling mechanism operable to bring a sample into close contact with a base of the prism;

a thermal controller adapted to regulate respective temperatures of the prism supports and the coupling mechanism;
a light source operable to direct incident light to the base of the prism; and
a detector positioned to receive from the prism output light having intensity variations, wherein at least one of sample thickness and refractive index may be determined from the intensity variations.

18. Apparatus according to claim 17, further comprising respective temperature sensors in contact with the prism and the coupling mechanism that provide the thermal controller with respective indications of respective temperatures of the prism and the coupling mechanism.

19. Apparatus according to claim 17, further comprising respective thermal elements in each of the prism supports and the coupling mechanism, wherein each said thermal element is coupled to the thermal controller and the thermal controller regulates the respective temperatures of the prism supports and the coupling mechanism via the respective thermal elements.

20. Apparatus according to claim 17, wherein the thermal controller is adapted to heat the sample to a temperature above room temperature.

21. Apparatus according to claim 17, wherein the thermal controller is adapted to cool the sample to a temperature below room temperature.

22. Apparatus for determining thickness and refractive index, comprising:
a prism having a base;
a sample support adapted to hold a sample in close contact with the prism base;
a thermal controller that regulates the temperature of the sample;
a first temperature sensor that provides to the thermal controller an indication of a current temperature of the sample support;
a light source operable to direct incident light to the base of the prism; and
a detector positioned to receive from the prism output light having intensity variations, wherein at least one of sample thickness and refractive index may be determined from the intensity variations.

23. Apparatus according to claim 22, wherein the thermal controller regulates respective temperatures of the prism and the sample support.

24. Apparatus according to claim 22, wherein the light source includes a monochromatic light source.

25. Apparatus according to claim 22, wherein the detector comprises an array of photodetector elements.

26. Apparatus according to claim 22, further comprising:
a second temperature sensor that provides to the thermal controller an indication of a current temperature of the prism, wherein the second temperature sensor comprises a thermocouple.

27. Apparatus according to claim 22, wherein the first temperature sensor comprises a thermocouple.

28. Apparatus according to claim 22, wherein the thermal controller enables the respective temperatures of the prism and the sample support to be set to a common temperature.

29. Apparatus according to claim 22, wherein the prism is disposed between a pair of prism supports, each of which is made of a thermally conductive material.

30. Apparatus according to claim 29, wherein the thermal controller is adapted to regulate the temperature of the prism by regulating respective temperatures of each of the prism supports.

31. Apparatus according to claim 30, wherein the thermal controller is adapted to regulate the respective temperatures of the prism supports via a respective thermal element in each of the prism supports.

32. Apparatus according to claim 31, wherein the prism supports are clamp jaws.

33. Apparatus according to claim 22, wherein the thermal controller is adapted to regulate the temperature of the sample support.

34. Apparatus according to claim 33, wherein the thermal controller is adapted to regulate the temperature of the sample support via a thermal element in the sample support.

35. Apparatus according to claim 22, wherein the thermal controller is adapted to heat the sample to a temperature above room temperature.

36. Apparatus according to claim 22, wherein the thermal controller is adapted to cool the sample to a temperature below room temperature.

37. Apparatus for determining thickness and refractive index, comprising:
a prism having a base, wherein the prism is disposed between a pair of prism supports, each of which is made of a thermally conductive material;
a sample support adapted to hold a sample in close contact with the prism base;
a thermal controller that regulates the temperature of the sample;
a temperature sensor that provides to the thermal controller an indication of a current temperature of the sample support;
a light source operable to direct incident light to the base of the prism; and
a detector positioned to receive from the prism output light having intensity variations, wherein at least one of sample thickness and refractive index may be determined from the intensity variations.

38. Apparatus according to claim 37, wherein the thermal controller regulates respective temperatures of the prism and the sample support.

39. Apparatus according to claim 37, wherein the light source includes a monochromatic light source.

40. Apparatus according to claim 37, wherein the detector comprises an array of photodetector elements.

41. Apparatus according to claim 37, further comprising:
a temperature sensor that provides to the thermal controller an indication of a current temperature of the prism, wherein the temperature sensor comprises a thermocouple.

42. Apparatus according to claim 37, further comprising:
a temperature sensor that provides to the thermal controller an indication of a current temperature of the sample support, wherein the temperature sensor comprises a thermocouple.

43. Apparatus according to claim 37, wherein the thermal controller enables the respective temperatures of the prism and the sample support to be set to a common temperature.

44. Apparatus according to claim 37, wherein the thermal controller is adapted to regulate the temperature of the prism by regulating respective temperatures of each of the prism supports.

45. Apparatus according to claim 44, wherein the thermal controller is adapted to regulate the respective temperatures of the prism supports via a respective thermal element in each of the prism supports.

46. Apparatus according to claim 45, wherein the prism supports are clamp jaws.

47. Apparatus according to claim 37, wherein the thermal controller is adapted to regulate the temperature of the sample support.

48. Apparatus according to claim 47, wherein the thermal controller is adapted to regulate the temperature of the sample support via a thermal element in the sample support.

49. Apparatus according to claim 37, wherein the thermal controller is adapted to heat the sample to a temperature above room temperature.

50. Apparatus according to claim 37, wherein the thermal controller is adapted to cool the sample to a temperature below room temperature.

* * * * *